United States Patent
Andjelic et al.

(10) Patent No.: US 10,300,165 B2
(45) Date of Patent: May 28, 2019

(54) SEGMENTED, P-DIOXANONE-RICH, POLY(P-DIOXANONE-CO-EPSILON-CAPROLACTONE) COPOLYMERS FOR MEDICAL APPLICATIONS AND DEVICES MADE THEREFROM

(71) Applicant: Ethicon, Inc., Somerville, NJ (US)

(72) Inventors: Sasa Andjelic, Nanuet, NY (US); Kenneth Keilman, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 674 days.

(21) Appl. No.: 15/001,313

(22) Filed: Jan. 20, 2016

(65) Prior Publication Data

US 2017/0202996 A1    Jul. 20, 2017

(51) Int. Cl.
| | | |
|---|---|---|
| *A61L 17/10* | (2006.01) | |
| *A61L 17/00* | (2006.01) | |
| *C08G 81/00* | (2006.01) | |
| *A61L 31/06* | (2006.01) | |
| *C08G 63/664* | (2006.01) | |

(52) U.S. Cl.
CPC .......... *A61L 17/105* (2013.01); *A61L 17/005* (2013.01); *A61L 31/06* (2013.01); *C08G 63/664* (2013.01); *C08G 81/00* (2013.01); *A61L 2300/404* (2013.01)

(58) Field of Classification Search
USPC ........................................................ 524/411
See application file for complete search history.

(56) References Cited

U.S. PATENT DOCUMENTS

| | | |
|---|---|---|
| 5,047,048 A | 9/1991 | Bezwada et al. |
| 5,133,739 A | 7/1992 | Bezwada et al. |
| 5,314,989 A | 5/1994 | Kennedy et al. |
| 5,522,841 A | 6/1996 | Roby et al. |
| 5,705,181 A | 1/1998 | Cooper et al. |
| 6,712,838 B2 | 3/2004 | D'Aversa et al. |
| 2013/0005829 A1 | 1/2013 | Jamiolkowski et al. |

*Primary Examiner* — Terressa Boykin
(74) *Attorney, Agent, or Firm* — David R. Crichton (57) ABSTRACT

Novel semi-crystalline, p-dioxanone-rich ABA triblock copolymers of p-dioxanone and epsilon-caprolactone, where "B" block is a random copolymer of p-dioxanone and epsilon-caprolactone, and absorbable devices for long term medical applications are disclosed. The novel polymer compositions are useful for long term absorbable surgical sutures, and other medical devices.

20 Claims, 2 Drawing Sheets

Figure 1. DSC Scan of the Second Heat Measurements for Non-Inventive Monofilament of Example 1B

Figure 2. DSC Scan of the Second Heat Measurements for Inventive Monofilament of Example 3B

SEGMENTED, P-DIOXANONE-RICH, POLY(P-DIOXANONE-CO-EPSILON-CAPROLACTONE) COPOLYMERS FOR MEDICAL APPLICATIONS AND DEVICES MADE THEREFROM

FIELD OF THE INVENTION

This invention relates to novel semi-crystalline, p-dioxanone-rich block copolymers of p-dioxanone and epsilon-caprolactone for long term absorbable medical applications, in particular, surgical sutures and hernia meshes.

BACKGROUND OF THE INVENTION

Synthetic absorbable polyesters are well known in the art. The open and patent literature particularly describe absorbable polymers and copolymers made from glycolide, L(−)-lactide, D(+)-lactide, meso-lactide, epsilon-caprolactone, p-dioxanone, and trimethylene carbonate. The term absorbable is meant to be a generic term, which may also include bioabsorbable, resorbable, bioresorbable, degradable or biodegradable.

One very important application of absorbable polyesters is their use as surgical sutures. Absorbable sutures generally come in two basic forms, multifilament braids and monofilament fibers. For a polymer to function as a monofilament, it must generally possess a glass transition temperature, $T_g$, below room temperature. A low $T_g$ helps to insure a low Young's modulus which in turn leads to filaments that are soft and pliable. A high $T_g$ material would result in a wire-like fiber that would lead to relatively difficult handling sutures; in this art such sutures would be referred to or described as having a poor "hand". If a polymer possesses a high $T_g$, and it is to be made into a suture, it invariably must be a construction based on multifilament yarns; a good example of this is a braid construction. It is known that monofilament sutures may have advantages versus multifilament sutures. Advantages of monofilament structures include a lower surface area, with less tissue drag during insertion into the tissue, with possibly less tissue reaction. Other advantages include no wicking into interstices between filaments in which bacteria can move and locate. There is some thought that infectious fluids might more easily move along the length of a multifilament construction through the interstices; this of course cannot happen in monofilaments. Monofilament fiber is generally easier to manufacture as there are none of the braiding steps usually associated with multifilament yarns.

Absorbable monofilaments sutures have been made from poly(p-dioxanone) and other low $T_g$ polymers. A very important aspect of any absorbable medical device is the length of time that its mechanical properties are retained in vivo. For example, in some surgical applications it is important to retain strength for a considerable length of time to allow the body the time necessary to heal while performing its desired function. Slowly healing situations include, for example, diabetic patients or bodily areas having poor blood supply. Absorbable long term sutures have been made from conventional polymers, primarily made from lactide. Examples include a braided suture made from a high-lactide, and lactide/glycolide copolymer. In this art, those skilled in the art will appreciate that it is clear that monofilament and multifilament absorbable sutures exist and that short term and long term absorbable sutures exist. What does not presently exist is an absorbable polymer that can be made into a suture that is soft enough to be made into a monofilament and maintain its properties post-implantation to function long term. There then remains a problem of providing such a polymer, and there is a need not only for such a polymer, but also a need for a suture made from such a polymer. It is to be understood that these polymers would also be useful in the construction of fabrics such as surgical meshes.

Beside the opportunities in long term sutures and meshes, there exists opportunities for such polymers in devices that must be made from a deformable resin, ideally fabricated by known and conventional methods such as and including injection molding.

Crystalline block copolymers of epsilon-caprolactone and p-dioxanone are disclosed in U.S. Pat. No. 5,047,048 (Bezwada et al.). The copolymers covered in the patent range from about 5 to about 40 weight percent epsilon-caprolactone and the absorption profile is similar to poly(p-dioxanone). Furthermore, this reference describes the copolymers of p-dioxanone and epsilon-caprolactone made in random or block, segmented configuration of both, A-B and A-B-A types. Segmented copolymers of A-B-A type contain middle section "B" made from 100% epsilon-caprolactone, while end-blocks "A" are made of polymerized p-dioxanone only. Monofilaments made from these copolymers exhibit mechanical and hydrolysis properties similar to p-dioxanone homopolymer, with Young's modulus of elasticity only slightly lower than the p-dioxanone homopolymer (100 percent polymerized p-dioxanone). It is expected that fibers made from these epsilon-caprolactone/p-dioxanone copolymers, rich in p-dioxanone, would retain their mechanical properties post-implantation similar to p-dioxanone homopolymer. There then remains a strong need for a material that exhibits significantly lower Young's modulus of elasticity (i.e., better pliability) than that exhibited by the copolymers of the '048 patent to allow fabrication into soft monofilament fibers useful as suture or mesh components. In addition, there is a need for a monofilament that could retain mechanical properties, such as Breaking Strength Retention (BSR), longer than that exhibited by the copolymers of the '048 patent.

US 2013/0005829 A1 (Jamiolkowski et al.) discloses segmented epsilon-caprolactone-rich poly(epsi/on-caprolactone-co-p-dioxanone) copolymers of A-B-A type for use in long-term absorbable medical applications. The main disadvantage of these copolymers is their low melting point temperature (55-60° C.), which may make them thermally and physically unstable during various processing and storage conditions where higher temperatures are present (e.g., EO sterilization, exposure to hot temperatures during shipping, etc.). In addition, initial strength of the monofilaments made from these copolymers is relatively low, and their BSR properties are much longer than practically needed. Although these polymers are useful, there is still need for a monofilament suture that exhibits high thermal stability, high initial strength, and favorable BSR properties.

U.S. Pat. No. 5,314,989 (Kennedy et al.), entitled "Absorbable Composition", describes a block copolymer for use in the fabrication of absorbable articles such as monofilament surgical sutures. The copolymer is prepared by copolymerizing one or more hard phase forming monomers and 1,4-dioxan-2-one, and then polymerizing one or more hard phase forming monomers with the dioxanone-containing copolymer. The materials of this invention require a hard phase, which is not within the scope of the present invention.

Similarly, U.S. Pat. No. 5,522,841 (Roby et al.), entitled "Absorbable Block Copolymers and Surgical Articles Fabricated Therefrom", describes absorbable surgical articles formed from a block copolymer having one of the blocks made from hard phase forming monomers and another of the blocks made from random copolymers of soft phase forming monomers. Hard phase forming monomers are said to include glycolide and lactide while soft phase forming monomers include 1,4-dioxane-2-one and 1,3-dioxane-2-one and caprolactone.

U.S. Pat. No. 5,705,181 (Cooper et al.), entitled "Method of Making Absorbable Polymer Blends of Polylactides, Polycaprolactone and Polydioxanone", describes absorbable binary and tertiary blends of homopolymers and copolymers of poly(lactide), poly(glycolide), poly(ε-caprolactone), and poly(p-dioxanone). These materials are blends and not copolymers.

There is a need in this art for novel, long term absorbable sutures that have good handling characteristics and strength retention. There is a further need in this art for novel absorbable polymer compositions for manufacturing such sutures and other absorbable medical devices.

SUMMARY OF THE INVENTION

Novel semi-crystalline, p-dioxanone-rich block copolymers of p-dioxanone and epsilon-caprolactone for long term absorbable medical applications are disclosed. The novel segmented, semicrystalline, synthetic, absorbable copolymers of the present invention consist of lactone monomers selected from the group consisting of p-dioxanone and epsilon-caprolactone, wherein the p-dioxanone is a major component. The absorbable copolymers have a structure A-B-A having end segments A and middle segment B, wherein end-segments A are polymerized p-dioxanone blocks and the middle segment B is a copolymer comprising a polymerized p-dioxanone-co-epsilon-caprolactone block. The middle segment B is fully amorphous and contains about 60 mole percent to about 90 mole percent of polymerized epsilon-caprolactone, and about 10 mole percent to about 40 mole percent of polymerized p-dioxanone. And, the total amount of polymerized p-dioxanone in the absorbable copolymer is between about 80 mole percent to about 95 mole percent.

We have unexpectedly discovered that monofilaments made from segmented, p-dioxanone-rich, poly(p-dioxanone-co-epsilon-caprolactone) copolymers of A-B-A type, where "B" block is a copolymer of p-dioxanone and epsilon-caprolactone (instead of 100 percent polymerized epsilon-caprolactone) exhibit exceptional softness and pliability (very low Young's modulus of elasticity) having, in most cases, longer Breaking Strength Retention properties (BSR) than either p-dioxanone homopolymer or poly(p-dioxanone-co-epsi/on-caprolactone) copolymers of A-B-A type, where "B" block is composed of 100 percent polymerized epsilon-caprolactone.

Another aspect of the present invention is an absorbable copolymer of the structure A-B-A having end segments A and middle segment B, wherein end-segments A are polymerized p-dioxanone blocks and the middle segment B is a copolymer made from epsilon-caprolactone and a minor amount of a lactone monomer selected from the group consisting of L(−)-lactide, D(+)-lactide, meso-lactide, and trimethylene. The middle segment B is fully amorphous and contains about 60 mole percent to about 95 mole percent of polymerized epsilon-caprolactone, and about 5 mole percent to about 40 mole percent of polymerized lactone monomer. And, the total amount of polymerized p-dioxanone in the absorbable copolymer is between about 80 mole percent to about 95 mole percent.

Another aspect of the present invention is a long term absorbable suture made from the above-described copolymer.

Yet another aspect of the present invention is an absorbable medical device made from the above described suture.

Still yet another aspect of the present invention is a method of manufacturing a medical device from said novel copolymers.

A further aspect of the present invention is a method of performing a surgical procedure wherein a medical device made from the novel copolymers of the present invention is implanted in tissue in a patient.

These and other aspects and advantages of the present invention will become more apparent from the following description and accompanying drawings.

DETAILED DESCRIPTION OF INVENTION

The present invention is directed towards copolymers of p-dioxanone and epsilon-caprolactone. More specifically, this class of copolymers rich in p-dioxanone is made to have a blocky sequence distribution that is non-random. In p-dioxanone/epsilon-caprolactone copolymers in which the majority of the material is based on p-dioxanone, the melting point would be high enough (above 100° C.) that would allow easy processing and high thermal stability useful in long-term suture applications. The compositions must be rich in p-dioxanone, e.g., having a polymerized p-dioxanone content of 80 percent or greater to allow for fast crystallization rates.

Dimensional stability in a fiber used to manufacture a surgical suture is very important to prevent shrinkage, both in the sterile package before use, as well as in the patient after surgical implantation. Dimensional stability in low glass transition ($T_g$) material can be achieved by crystallization of the formed article. Regarding the phenomena of crystallization of copolymers, a number of factors play important roles. These factors include overall chemical composition and the sequence distribution.

Although the overall level of crystallinity (and the $T_g$ of the material) plays a role in dimensional stability, it is important to realize that the rate of crystallization is critical to processing. If a low $T_g$ material is processed and it rate of crystallization is very slow, it is very difficult to maintain dimensional tolerances since shrinkage and warpage easily occur. Fast crystallization is thus an advantage. To increase the rate of crystallization of a copolymer of given overall chemical composition, a block structure, particularly of A-B-A type would be preferable over a random sequence distribution. However, achieving this with the two lactone monomers p-dioxanone and epsilon-caprolactone is known to be very difficult.

Poly(p-dioxanone) has a low ceiling temperature, accordingly at elevated temperatures it tends to exist with a high fraction of monomer at equilibrium. When starting with fully polymerized material at elevated temperatures, it "depolymerizes" thereby resulting in a combination of polymer and regenerated monomer. Regenerated equilibrium monomer levels for poly(p-dioxanone) can be rather high, approaching 30 to 50 percent at reaction temperatures of 110 to 160° C.

On the other hand, it is quite difficult to polymerize epsilon-caprolactone at temperatures lower than about 160° C. There then exists a problem as to how to achieve polymerization of these two co-monomers to produce a block structure with high enough molecular weight so as to result in products having good mechanical properties.

The novel copolymers of the present invention are prepared by first polymerizing all the epsilon-caprolactone monomers and a small amount of p-dioxanone monomers at temperatures between about 170° C. and about 240° C. Temperatures between about 185 and about 195° C. are particularly advantageous. Although a monofunctional alcohol such as dodecanol might be used for initiation, a diol such as diethylene glycol has been found to work well. Combinations of mono-functional and di-functional, or multifunctional conventional initiators may also be used. Reaction times can vary with catalyst level. Suitable catalysts include conventional catalysts such as stannous octoate. The catalyst may be used at a monomer/catalyst level ranging from about 10,000/1 to about 300,000/1, with a preferred level of about 25,000/1 to about 100,000/1. After the completion of this first stage of the polymerization, the temperature is lowered substantially with preferably all epsilon-caprolactone monomer fully polymerized, while some amount of p-dioxanone monomer would still remain unreacted due to thermodynamic equilibrium. Once the temperature is lowered, for example to 150° C., the major part of p-dioxanone monomer can be added to the reactor; this can be conveniently done by pre-melting this p-dioxanone monomer and adding it in a molten form. Once the p-dioxanone monomer is added, the temperature is brought to about 110° C. to complete the co-polymerization.

Alternately, once the major portion of p-dioxanone monomer is added, the temperature can be brought to about 110° C., maintained at this temperature for some period of time (e.g., about 3 to 4 hours), followed by polymer discharge into suitable containers for subsequent low temperature polymerization (e.g., 80° C.) for an extended period of time to complete the co-polymerization. Higher monomer-to-polymer conversions may be possible utilizing this alternate low temperature finishing approach.

It will be clear to one skilled in the art that various alternate polymerization approaches are possible and still produce the copolymer of the subject invention. One might then consider a process in which the reaction temperature after the initial stage of copolymerizing the epsilon-caprolactone and p-dioxanone is dropped immediately to 110° C. prior to the addition of the major portion of p-dioxanone monomer. Again, one skilled in the art can provide a variety of alternate polymerization schemes.

Poly(epsi/on-caprolactone-co-p-dioxanone) copolymers rich in polymerized p-dioxanone having levels of incorporated epsilon-caprolactone greater than about 20 mole percent are unsuitable for copolymers of the present invention because of crystallization difficulties. Poly(epsilon-caprolactone-co-p-dioxanone) copolymers comprising a polymerized p-dioxanone having a molar level between 80 percent to 95 percent and a polymerized epsilon-caprolactone molar level between 5 percent to 20 percent are useful in the practice of the present invention. This class of copolymers, the poly(epsilon-caprolactone-co-p-dioxanone) family rich p-dioxanone, will preferably contain about 10 mole percent to about 20 mole percent of polymerized epsilon-caprolactone.

The copolymers of the subject invention are semicrystalline in nature, having a crystallinity level ranging typically from about 25 to about 50 percent, more typically about 30 to about 45 percent. The copolymers will have a molecular weight sufficiently high to allow the medical devices formed therefrom to effectively have the mechanical properties needed to perform their intended function. For instance, for a melt-blown nonwoven structure the molecular weight may be a little lower, and for extruded fibers, they may be a little higher. Typically, for example, the molecular weight of the copolymers of the subject invention will be such so as to exhibit inherent viscosities as measured in hexafluoroisopropanol (HFIP, or hexafluoro-2-propanol) at 25° C. and at a concentration of 0.1 g/dL between about 0.5 dL/g to about 2.5 dL/g. The surgical sutures made from the novel copolymers of the present invention preferably are monofilaments with a Young's modulus of less than about 160,000 psi. In one embodiment, the copolymer has a glass transition temperature below about 0° C. The novel copolymers of the present invention will preferably have an absorption time between about 6 and about 24 months.

In one embodiment, the medical devices made of the copolymers of the present invention may contain conventional active ingredients, such as antimicrobials, antibiotics, therapeutic agents, hemostatic agents, radio-opaque materials, tissue growth factors, and combinations thereof. In one embodiment the antimicrobial is Triclosan, PHMB, silver and silver derivatives or any other bio-active agent.

The copolymers of the subject invention can be melt extruded by a variety of conventional means. Monofilament fiber formation can be accomplished by melt extrusion followed by extrudate drawing with or without annealing. Multifilament fiber formation is possible by conventional means. Methods of manufacturing monofilament and multifilament braided sutures are disclosed in U.S. Pat. No. 5,133,739, entitled "Segmented Copolymers of epsilon-Caprolactone and Glycolide" and U.S. Pat. No. 6,712,838 entitled "Braided Suture with Improved Knot Strength and Process to Produce Same", are incorporated by reference herein in their entirety.

The copolymers of the present invention may be used to manufacture conventional medical devices in addition to sutures using conventional processes. For example, injection molding might be accomplished after allowing the copolymer to crystallize in the mold; alternately, biocompatible nucleating agents might be added to the copolymer to reduce cycle time. The medical devices may include, in addition to meshes, the following conventional devices meshes, tissue repair fabrics, suture anchors, stents, orthopedic implants, staples, tacks, fasteners, suture clips, etc.

Sutures made from the copolymers of the present invention may be used in a conventional manner in conventional surgical procedures, e.g., to approximate tissue or affix tissue to medical devices. Typically, after a patient is prepared for surgery in a conventional manner, including swabbing the outer skin with antimicrobial solutions and anesthetizing the patient, the surgeon will make the required incisions, and, after performing the required procedure proceed to approximate tissue using the long-term absorbable sutures of the present invention (in particular monofilament sutures) made from the novel copolymers of the present invention. In addition to tissue approximation, the sutures may be used to affix implanted medical devices to tissue in a conventional manner. After the incisions are approximated, and the procedure is completed, the patient is then moved to a recovery area. The long-term absorbable sutures of the present invention in the patient retain their strength in vivo for the required time to allow effective healing and recovery.

Poly(p-dioxanone) is a low Tg (−11° C.) semi-crystalline polyester resin finding extensive utility as a suture material and as injection molded implantable medical devices. It will be understood by one having ordinary skill in the art that the level of crystallinity needed to achieve dimensional stability in the resulting devices will depend on the glass transition temperature of the (co)polymer. That is, to avoid fiber shrinkage and other consequences of dimensional instability, it is important to provide some level of crystallinity to counteract the phenomena. The level of crystallinity that is needed for a particular material of given glass transition temperature with given molecular orientation can be experimentally determined by one having ordinary skill in the art. The level for crystallinity required to achieve dimensional stability in monofilaments may be a minimum of about 25 percent in polymeric materials possessing glass transition temperatures below 0° C.

Besides the level of crystallinity, the rate of crystallization is very important in the monofilament extrusion process. If a material crystallizes too slowly, especially if it possesses a glass transition temperature below room temperature, the resulting fiber product may have frequent breaks, low strength, and low molecular orientation. A slow-to-crystallize (co)polymer will be quite difficult to process into monofilaments with desired physical properties.

It would be advantageous to have a material exhibiting a greater reversible extensibility (i.e., elasticity) and a significantly lower modulus than poly(p-dioxanone). Certain p-dioxanone-rich copolymers are particularly useful for this application. Specifically, an 81/19 mole/mole poly(p-dioxanone-co-epsilon-caprolactone) copolymer [81/19 PDO/Cap] was prepared in a sequential addition-type of polymerization starting with a first stage charge of 66 mole percent of epsilon-caprolactone and 34 mole percent of p-dioxanone, followed by a subsequent second stage of major p-dioxanone addition. The total initial charge was 85/15 mole/mole p-dioxanone/epsilon-caprolactone. See Example 4 for the details of this copolymerization.

Poly(p-dioxanone-co-epsilon-caprolactone) copolymers rich in polymerized p-dioxanone having levels of incorporated epsilon-caprolactone greater than about 20 mole percent are unsuitable for the present application, because it is difficult to prepare monofilaments from such copolymers having good mechanical properties. It is speculated that this may be because p-dioxanone-rich (p-dioxanone-co-epsilon-caprolactone) copolymers having greater than about 20 mole percent of incorporated epsilon-caprolactone exhibit too low an elastic modulus and low overall crystallinity resulting in a loss of molecular orientation leading to lower strength fibers. See Example 6 for the synthesis and processing details of this high epsilon-caprolactone copolymer.

As discussed herein, suitable synthetic absorbable polymers for the present invention include p-dioxanone/epsilon-caprolactone segmented A-B-A type copolymers rich in p-dioxanone, wherein the "B" segment is a copolymer of epsilon-caprolactone and a minor amount of p-dioxanone. This "B" copolymer segment will typically contain between 10 mole percent and 40 mole percent of polymerized p-dioxanone to effectively scramble the epsilon-caprolactone sequence distribution, making the "B" block fully amorphous. Within this class, the copolymers rich in polymerized p-dioxanone will typically have between about 80 to about 95 mole percent of total polymerized p-dioxanone in the final copolymer.

Alternatively, the "B" segment may represent a copolymer of epsilon-caprolactone and a minor amount of other lactone monomer instead of, or in addition to p-dioxanone. Preferably, for long-term medical applications, these lactone monomers may be taken from the group of L(−)-lactide, D(+)-lactide, meso-lactide, and trimethylene carbonate. Such "B" copolymer segment will typically contain between 5 mole percent and 40 mole percent of polymerized lactone monomers other than epsilon-caprolactone to effectively scramble the epsilon-caprolactone sequence distribution, making the "B" block fully amorphous.

If, for instance, p-dioxanone/epsi/on-caprolactone segmented A-B-A type copolymers rich in p-dioxanone contain a mid-block "B" composed of 100 mole percent epsilon-caprolactone, the resulting "B" block would be crystalline. This would increase the Young's modulus of elasticity, making the monofilaments made from this copolymer stiffer and less pliable. This class of polymers, the poly(p-dioxanone-co-epsilon-caprolactone) family rich p-dioxanone where both segments "A" and "B" are crystalline, are described previously in the prior art ('048), as well as in our non-inventive Examples 1 and 2.

The medical devices made from the copolymers of the present invention may contain if desired medically useful substances. The medically useful substances may be incorporated into or onto the medical devices in a variety of conventional manners including compounding, coating, spraying, dipping, sputtering and the like. In addition, monofilament sutures made from the copolymers of the present invention may be delivered to the surgeon in a variety of lengths. Preferably, conventional surgical needles are mounted to one end or both ends of the sutures (i.e., single-armed or double-armed), although the sutures may be unarmed with no surgical needles mounted.

If desired, the medical devices of the present invention may contain other conventional medically useful components and agents. The other components, additives or agents will be present to provide additional desired characteristics to the monofilament sutures and other medical devices of the present invention including but not limited to antimicrobial characteristics, controlled drug elution, therapeutic aspects, radio-opacification, and enhanced osseointegration.

The surgical sutures of the copolymers of the present invention may also include other conventional additives including dyes, radio-opaque agents, growth factors and the like. The dyes should be generally acceptable for clinical use with absorbable polymers; this includes, without limitation, D&C Violet No. 2 and D&C Blue No. 6 and similar combinations thereof. Additional dyes that are useful include conventional dyes useful with absorbable polymers including D&C Green No. 6, and D&C Blue No. 6.

The variety of therapeutic agents that can be used in the copolymers and medical devices of the present invention is vast. In general, therapeutic agents which may be administered via compositions of the invention include, without limitation, anti-infectives, such as antibiotics and antiviral agents.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents useful with the sutures of the present invention include the polychlorophenoxy phenols such as 5-chloro-2-(2,4-dichlorophenoxy)phenol (also known as Triclosan). Examples of radio-opacification agents include barium sulfate while examples of osseointegration agents include tricalcium phosphate.

The variety of therapeutic agents that can be used with the medical devices of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics that may be incorporated into the medical devices of the present invention include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Modern surgical sutures generally range from Size 5 (heavy braided suture for orthopedics) to Size 11/0 (for example, a fine monofilament suture for ophthalmics). The actual diameter of thread for a given U.S.P. size differs depending on the suture material class. The diameters of sutures in the synthetic absorbable suture class are listed in the United States Pharmacopeia (USP) as well as in the European Pharmacopoeia. The USP standard is more commonly used. The novel sutures of the present invention can be made in a variety of sizes, including conventional suture sizes. The suture sizes of the monofilament sutures of the present invention will range from 10-0 to 5. The monofilament fibers of the present invention when used for constructing other medical devices such as meshes, etc., will typically have diameters in the range of about 1 to about 8 mils. Multifilament sutures when constructed from the fibers of the present invention will have a sufficiently effective denier per filament (dpf) to provide the desired properties, typically a dpf of about 0.5 to about 5.

The novel monofilament sutures of the present invention may be packaged in conventional suture packaging including polymer tray with tracks, paper folders, etc., with a polymer and/or foil overwrap that is hermetically sealed and impervious to moisture and microbes. The sutures will be sterilized preferably in their packages using conventional medical device sterilizations processes, such as ethylene oxide, radiation, autoclaving, etc. Those skilled in the art will understand that the optimal sterilization process chosen will not adversely affect the characteristics of the absorbable polymeric sutures.

The novel absorbable sutures of the present invention that are made from the novel absorbable copolymers are preferably useful as monofilament surgical sutures. However, the filaments may be used in other conventional medical devices including, but not limited to, fibrous devices such as multifilament-based sutures and surgical fabrics including meshes, woven fabrics, nonwoven fabrics, knitted fabrics, fibrous bundles, cords, tissue engineering substrates, and the like. The surgical meshes may be made using conventional methods including knitting, weaving, air-laying, etc.

Medical devices made from the novel segmented copolymers of the present invention may be used in conventional surgical procedures using conventional surgical techniques. For example, monofilament surgical sutures made from the novel copolymers of the present invention that are mounted to conventional surgical sutures may be used to suture wounds, repair blood vessels and organs, close incisions, attach medical devices to tissue, etc. In the case of repairing wounds or closing incisions by approximating tissue edges about a wound or incision, the needle and suture are passed through tissue about the wound or incision one or more times, and the sides of the wound are brought together by tensioning the suture and securing it in place in a conventional manner such as with knots.

If desired, the monofilament sutures of the copolymers of the present invention may be processed to have barbs. Such barbs can be emplaced or incorporated in a conventional manner including cutting, molding, pre-forming, forming, attaching, etc. An example of a barb-forming process is disclosed in the U.S. Pat. No. 8,216,497 "Tissue Holding Devices and Methods for Making the Same" which is incorporated herein by reference. An alternate process of making barbed sutures is a cutting process. An example of a barb-cutting process is disclosed in the U.S. Pat. No. 7,913,365 "Method of Forming Barbs on a Suture and Apparatus for Performing Same" which is incorporated herein by reference.

The following examples are illustrative of the principles and practice of this invention, although not limited thereto. Numerous additional embodiments within the scope and spirit of the invention will become apparent to those skilled in the art once having the benefit of this disclosure.

In the present disclosure, calorimetric results were generated on a TA Instruments Differential Scanning calorimeter, Model 2910 MDSC, using dry $N_2$ as a purge gas. Both non-isothermal and isothermal crystallization studies were conducted. In non-isothermal conditions, after melting of the copolymers at 140° C. for three minutes, the copolymers were cooled under a controlled rate; or, after melting, the copolymer was quenched below its glass transition temperature, then heated under a controlled heating rate of 10° C./min.

Some supporting evidence was obtained by conventional Wide Angle X-Ray Diffraction (WAXD) analysis. The WAXD measurements of the isothermally grown films were carried out on a Siemens Hi-Star™ unit using CuKα radiation at the wavelength of 1.542 Å. The instrument was operated at 40 kV and 40 mA with the collimator size of Ø

0.5 mm. The convolution of the X-ray images and the calculation of crystallinity content were conducted using the DIFFRAC PLUS™ software developed by Siemens.

In vitro BSR measurements for Examples 1B-Annealed, 2B-Annealed, 3B-Annealed, 4B-Annealed, and PDS II as a control were conducted at physiologically relevant in vitro conditions: 7.27 pH buffer solution maintained at 37° C. temperature. The data was used for BSR evaluations in pounds and percentages. At specified time points, the tensile strength of samples was tested using Instron material testing machine. The test parameters were 1 inch gauge length and 1 inch per minute crosshead speed.

Example 1A (Non-Inventive)

Synthesis of Segmented p-Dioxanone-Rich Poly(p-Dioxanone-Co-Epsilon-Caprolactone) A-B-A Triblock Copolymer at 79/21 by Mole, Wherein the "B" Segment is Composed of Polymerized Epsilon-Caprolactone Only Using a 10-gallon stainless steel oil jacketed reactor equipped with agitation, 4,086 grams of epsilon-caprolactone were added along with 28.14 grams of diethylene glycol, 20.66 mL of a 0.33M solution of stannous octoate in toluene, and 12.4 grams of D&C Violet #2 dye. After the initial charge, a purging cycle with agitation at a rotational speed of 6 RPM in an upward direction was conducted. The reactor was evacuated to pressures less than 550 mTorr followed by the introduction of nitrogen gas. The cycle was repeated once again to ensure a dry atmosphere. At the end of the final nitrogen purge, the pressure was adjusted to be slightly above one atmosphere. The vessel was heated by setting the oil controller at 195° C. at a rate of 180° C. per hour. The reaction continued for 2 hours from the time the oil temperature reached 195° C.

In the next stage, the oil controller set point was decreased first to 150° C., and 20,689 grams of molten p-dioxanone monomer was added from a melt tank with an agitator speed of 10 RPM. The reactor temperature was then lowered to 110° C. for the rest of the reaction with the agitator speed at 7.5 RPM for 180 minutes. At the end of the reaction, the agitator speed was reduced to 5 RPM, and the polymer was discharged from the vessel into suitable containers. The containers were placed into a nitrogen oven set at 80° C. overnight to allow the copolymer to crystallize. During this step, the constant nitrogen flow was maintained in the oven to reduce possible moisture-induced degradation.

The crystallized polymer was then removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The granules were then sieved to remove any "fines" and weighed. The net weight of the ground and sieved polymer was 18.1 kg, which was next placed into a 3 cubic foot Patterson-Kelley tumble dryer to remove any residual monomer. The dryer was closed and the pressure was reduced to less than 200 mTorr. Once the pressure was below 200 mTorr, dryer rotation was activated at a rotational speed of 5-10 RPM with no heat for 10 hours. After 10 hours, the oil temperature was set to 80° C. at a heat up rate of 120° C. per hour. The oil temperature was maintained at approximately 80° C. for a period of 32 hours. At the end of the heating period, the batch was allowed to cool for a period of 3 hours while maintaining rotation and vacuum. The polymer was discharged from the dryer by pressurizing the vessel with nitrogen, opening the discharge valve, and allowing the polymer granules to descend into waiting vessels for long term storage.

The long term storage vessels were air tight and outfitted with valves allowing for evacuation so that the resin was stored under vacuum. The dried resin exhibited an inherent viscosity of 1.43 dL/g, as measured in hexafluoroisopropanol at 25° C. and at a concentration of 0.10 g/dL. Gel permeation chromatography analysis showed a weight average molecular weight of approximately 55,900 Daltons. Nuclear magnetic resonance analysis confirmed that the resin contained 78.9 mole percent poly(p-dioxanone) and 20.9 mole percent poly(epsilon-caprolactone) with a residual monomer content of less than 1.0 percent. The dried polymer was stored under vacuum until ready for use or evaluation.

Example 1B (Non-Inventive)

Monofilament Extrusion of the Segmented p-Dioxanone-Rich Poly(p-Dioxanone-Co-Epsilon-Caprolactone) Triblock Copolymer of Example 1A (79/21 by Mole)

The copolymer of Example 1A was extruded using a single-screw Davis-Standard one inch extruder with a 24:1 barrel length equipped with a single grooved feed throat. The die had a diameter of 40 mils and an L/D of 5/1; the die temperature was 125° C. After passing through an air gap of ¼ inch, the extrudate was quenched in a 20° C. water bath.

The fiber line was directed toward a first set of unheated godet rolls at a linear speed of 20 fpm. The fiber line was then directed toward a second set of unheated godet rolls operating at 125 fpm. The fiber line was then directed through a 6-foot hot air oven at 80° C. to a third set of unheated godet rolls; this set of rolls was operating at 180 fpm. The line was then directed through a second 6-foot hot air oven at 80° C. to a fourth set of unheated godet rolls. This last set of rolls was operating at 153 fpm, which is a lower speed than the previous set of godet rollers allowing the fiber to relax slightly (15.0%). The overall draw ratio was 7.65.

Such produced monofilament did not show promising results. During the extrusion process, the fiber would randomly become stiffer and more opaque. The dye cracking was also frequently observed. A considerable number of line breaks were experienced, especially at higher oven temperatures. The fiber was annealed at 85° C. for six hours on straight rack (0% rack relaxation).

Example 2A (Non-Inventive)

Synthesis of Segmented p-Dioxanone-Rich Poly(p-Dioxanone-Co-Epsilon-Caprolactone) A-B-A Triblock Copolymer at 83/17 by Mole, Wherein the "B" Segment is Composed of Polymerized Epsilon-Caprolactone Only Using a 10-gallon stainless steel oil jacketed reactor equipped with agitation, 4,123 grams of epsilon-caprolactone were added along with 63.9 grams of diethylene glycol and 16.58 mL of a 0.33M solution of stannous octoate in toluene. The reaction conditions in the first stage were closely matched to those in Example 1A.

In the second, copolymerization stage, the oil controller set point was decreased to 150° C., and 20,877 grams of molten p-dioxanone monomer were added from a melt tank with the agitator rotating at 10 RPM. The oil controller was then set to 110° C. for the rest of the reaction which lasted another 240 minutes. For this copolymer, the post-curing stage in a nitrogen purged oven at 80° C. for 4 days was conducted to drive conversion of p-dioxanone monomer through to completion. The grounding and sieving procedures were conducted according to Example 1A. The net weight of the ground and sieved polymer was 19.18 kg, which was then placed into a 3 cubic foot Patterson-Kelley tumble dryer for monomer removal following the conditions described in the Example 1A.

The dried resin exhibited an inherent viscosity of 1.20 dL/g, as measured in hexafluoroisopropanol at 25° C. and at a concentration of 0.10 g/dL. Gel permeation chromatography analysis showed a weight average molecular weight of approximately 43,100 Daltons. Nuclear magnetic resonance analysis confirmed that the resin contained 83.0 mole percent poly(p-dioxanone) and 16.6 mole percent poly(epsilon-caprolactone) with a residual monomer content of less than 1.0 percent.

Example 2B (Non-Inventive)

Monofilament Extrusion of the Segmented p-Dioxanone-Rich Poly(p-Dioxanone-Co-Epsi/On-Caprolactone) Triblock Copolymer of Example 2A (83/17 by Mole)

The copolymer of Example 2A was extruded using a single-screw Jenkins one inch extruder with an 18:1 barrel length equipped with a single grooved feed throat. The die had a diameter of 40 mils and an L/D of 5/1; the die temperature was 115° C. After passing through an air gap of ¼ inch, the extrudate was quenched in a 22° C. water bath.

The fiber line was directed toward a first set of unheated godet rolls at a linear speed of 12 fpm. The fiber line was then directed toward a second set of unheated godet rolls operating at 47 fpm. The fiber line was then directed through a 6-foot hot air oven at 85° C. to a third set of unheated godet rolls; this set of rolls was operating at 84 fpm. The line was then directed through a second 6-foot hot air oven at 95° C. to a fourth set of unheated godet rolls. This last set of rolls was operating at 74 fpm, which is a lower speed than the previous set of godet rollers allowing the fiber to relax slightly (11.9%). The overall draw ratio was 6.17.

This monofilament also did not show satisfactory results. During the extrusion process the fiber broke multiple times, and showed increased stiffness with higher draw ratios. The fiber was also annealed at 85° C. for six hours on straight rack (0% rack relaxation).

Example 3A (Inventive)

Synthesis of Segmented p-Dioxanone-Rich Poly(p-Dioxanone-Co-Epsilon-Caprolactone) A-B-A Triblock Copolymer at 85/15 by Mole, Wherein the "B" Segment is Composed 66 Mole % Polymerized Epsilon-Caprolactone and 34 Mole % Polymerized p-Dioxanone Using a 10-gallon stainless steel oil jacketed reactor equipped with agitation, 3,318 grams of epsilon-caprolactone and 1,482 grams of p-dioxanone were added along with 34.27 grams of diethylene glycol, 25.17 mL of a 0.33M solution of stannous octoate in toluene, and 15.0 grams of D&C Violet #2 dye. After the initial charge, a purging cycle with agitation at a rotational speed of 6 RPM in an upward direction was conducted. The reactor was evacuated to pressures less than 550 mTorr followed by the introduction of nitrogen gas. The cycle was repeated once again to ensure a dry atmosphere. At the end of the final nitrogen purge, the pressure was adjusted to be slightly above one atmosphere. The vessel was heated by setting the oil controller at 195° C. at a rate of 180° C. per hour. The reaction continued for 2 hours from the time that the oil temperature reached 195° C.

In the next stage, the oil controller set point was decreased first to 150° C., and 25,200 grams of molten p-dioxanone monomer were added from a melt tank with an agitator speed of 10 RPM. The reactor temperature was than lowered to 110° C. for the rest of the reaction with the agitator speed at 7.5 RPM in a forward direction for 180 minutes. At the end of the reaction, the agitator speed was reduced to 5 RPM, and the polymer was discharged from the vessel into suitable containers. The containers were placed into a nitrogen oven set at 80° C. overnight to allow copolymer to crystallize. During this step, the constant nitrogen flow was maintained in the oven to reduce possible moisture-induced degradation.

The crystallized polymer was then removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The granules were then sieved to remove any "fines" and weighed. The net weight of the ground and sieved polymer was 19.93 kg, which was next placed into a 3 cubic foot Patterson-Kelley tumble dryer to remove any residual monomer. The dryer was closed and the pressure was reduced to less than 200 mTorr. Once the pressure was below 200 mTorr, dryer rotation was activated at a rotational speed of 5-10 RPM with no heat for 10 hours. After 10 hours, the oil temperature was set to 80° C. at a heat up rate of 120° C. per hour. The oil temperature was maintained at approximately 80° C. for a period of 32 hours. At the end of the heating period, the batch was allowed to cool for a period of 3 hours while maintaining rotation and vacuum. The polymer was discharged from the dryer by pressurizing the vessel with nitrogen, opening the discharge valve, and allowing the polymer granules to descend into waiting vessels for long term storage.

The long term storage vessels were air tight and outfitted with valves allowing for evacuation so that the resin was stored under vacuum. The dried resin exhibited an inherent viscosity of 1.86 dL/g, as measured in hexafluoroisopropanol at 25° C. and at a concentration of 0.10 g/dL. Gel permeation chromatography analysis showed a weight average molecular weight of approximately 87,500 Daltons. Nuclear magnetic resonance analysis confirmed that the resin contained 84.8 mole percent poly(p-dioxanone) and 14.7 mole percent poly(epsilon-caprolactone) with a residual monomer content of less than 1.0 percent. The dried polymer was stored under vacuum until ready for use or evaluation.

Example 3B (Inventive)

Monofilament Extrusion of the Segmented p-Dioxanone-Rich Poly(p-Dioxanone-Co-Epsilon-Caprolactone) Triblock Copolymer of Example 3A (85/15 by Mole, with "B" Block Composition Cap/PDO 66/34 by Mole)

The copolymer of Example 3A was extruded using a single-screw Jenkins one inch extruder with an 18:1 barrel length equipped with a single grooved feed throat. The die had a diameter of 60 mils and an L/D of 5/1; the die temperature was 135° C. After passing through an air gap of ¾ inch, the extrudate was quenched in a 20° C. water bath.

After exiting water bath, the fiber was subjected to two different conditions. Under the first condition, no air quench cabinet was used like in the previous examples, and for the second condition, the undrawn fiber went through an air quench cabinet heated at 85° F. with one passage (wrap). It was observed that there was practically no difference in the final fiber physical properties when subjected to these two conditions. The fiber line was then directed toward a first set of unheated godet rolls at a linear speed of 20 fpm. The fiber line was then directed toward a second set of unheated godet rolls operating at 110 fpm. The fiber line was then directed through a 6-foot hot air oven at 85° C. to a third set of unheated godet rolls; this set of rolls was operating at 140 fpm. The line was then directed through a second 6-foot hot air oven at 95° C. to a fourth set of unheated godet rolls. This last set of rolls was operating at 126 fpm, which is a lower speed than the previous set of godet rollers allowing the fiber to relax slightly (10%). The overall draw ratio was 6.30 for the fiber made without air quench cabinet, and 5.85 for the process with the air quench cabinet used.

This monofilament extrusion went smoothly with only occasional breaks for the resin of Example 3A. Prior to testing, the fiber was also annealed at 85° C. for six hours on straight rack (0% rack relaxation).

Example 4A (Inventive)

Synthesis of Segmented p-Dioxanone-Rich Poly(p-Dioxanone-Co-Epsilon-Caprolactone) A-B-A Triblock Copolymer at 81/19 by Mole, Wherein the "B" Segment is Composed 66 Mole % Polymerized Epsilon-Caprolactone and 34 Mole % Polymerized p-Dioxanone Using a 10-gallon stainless steel oil jacketed reactor equipped with agitation, 4,947 grams of epsilon-caprolactone and 2,211 grams of p-dioxanone were added along with 38.33 grams of diethylene glycol, 25.2 mL of a 0.33M solution of stannous octoate in toluene, and 15.0 grams of D&C Violet #2 dye. After the initial charge, a purging cycle with agitation at a rotational speed of 6 RPM in an upward direction was conducted. The reactor was evacuated to pressures less than 550 mTorr followed by the introduction of nitrogen gas. The cycle was repeated once again to ensure a dry atmosphere. At the end of the final nitrogen purge, the pressure was adjusted to be slightly above one atmosphere. The vessel was heated by setting the oil controller at 195° C. at a rate of 180° C. per hour. The reaction continued for 3 hours from the time the oil temperature reached 195° C.

In the next stage, the oil controller set point was decreased first to 150° C., and 22,842 grams of molten p-dioxanone monomer was added from a melt tank with the agitator speed of 10 RPM. The reactor temperature was than lowered to 110° C. for the rest of the reaction with an agitator speed of 7.5 RPM in forward direction for 180 minutes. At the end of the reaction, the agitator speed was reduced to 5 RPM, and the polymer was discharged from the vessel into suitable containers. The containers were placed into a nitrogen oven set at 80° C., and the large portion of the produced resin (20.05 kg) was cured in the solid state for additional 85 hours. During this step, the constant nitrogen flow was maintained in the oven to reduce possible moisture-induced degradation.

The polymer was then removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The granules were then sieved to remove any "fines" and weighed. The net weight of the ground and sieved polymer was 19.36 kg, which was next placed into a 3 cubic foot Patterson-Kelley tumble dryer to remove any residual monomer. The drying procedure was identical to the procedures in the previous examples.

The resin was stored under vacuum. The dried resin exhibited an inherent viscosity of 1.20 dL/g, as measured in hexafluoroisopropanol at 25° C. and at a concentration of 0.10 g/dL. Gel permeation chromatography analysis showed a weight average molecular weight of approximately 40,000 Daltons. Nuclear magnetic resonance analysis confirmed that the resin contained 81.1 mole percent poly(p-dioxanone) and 18 mole percent poly(epsilon-caprolactone) with a residual monomer content of less than 1.0 percent. The dried polymer was stored under vacuum until ready for use or evaluation.

Example 4B (Inventive)

Monofilament Extrusion of the Segmented p-Dioxanone-Rich Poly(p-Dioxanone-Co-Epsilon-Caprolactone) Triblock Copolymer of Example 4A (81/19 by Mole, with "B" Block Composition Cap/PDO 66/34 by Mole)

The copolymer of Example 4A was extruded using a single-screw Davis-Standard one inch extruder with a 24:1 barrel length equipped with a single grooved feed throat. The die had a diameter of 60 mils and an L/D of 5/1; the die temperature was 110° C. After moving through an air gap of ¼ inch, the extrudate was quenched in a 20° C. water bath.

After exiting the water bath, the fiber went to an air quench cabinet maintained at room temperature (77° F.) with three wraps. The fiber line was then directed toward a first set of unheated godet rolls at a linear speed of 20 fpm. The fiber line next went through a 4-foot hot air oven at 90° C. located right between first and second sets of godets. The fiber line was then directed toward a second set of heated godet rolls at 80° C. operating at 132 fpm. The fiber line was then directed through a 6-foot hot air oven at 85° C. to a third set of unheated godet rolls; this set of rolls was operating at 140 fpm. The line was then directed through a second 6-foot hot air oven at 85° C. to a fourth set of unheated godet rolls. This last set of rolls was operating at 127 fpm, which is a lower speed than the previous set of godet rollers allowing the fiber to relax slightly (9.3%). The overall draw ratio was 6.35.

This monofilament extrusion for the resin of Example 4A went very smoothly with no breaks using different processing conditions. Prior to testing, the fiber was also annealed at 85° C. for six hours on straight rack (0% rack relaxation).

Example 5 (Inventive)

Synthesis of Segmented p-Dioxanone-Rich Poly(p-Dioxanone-Co-Epsilon-Caprolactone) A-B-A Triblock Copolymer at 93/7 by Mole, Wherein the "B" Segment is Composed 66 Mole % Polymerized Epsilon-Caprolactone and 34 Mole % Polymerized p-Dioxanone Using a 10-gallon stainless steel oil jacketed reactor equipped with agitation, 1,669 grams of epsilon-caprolactone and 746 grams of p-dioxanone were added along with 38.8 grams of diethylene glycol, 25.3 mL of a 0.33M solution of stannous octoate in toluene, and 15.0 grams of D&C Violet #2 dye. After the initial charge, a purging cycle with agitation at a rotational speed of 6 RPM in an upward direction was conducted. The reactor was evacuated to pressures less than 550 mTorr followed by the introduction of nitrogen gas. The cycle was repeated once again to ensure a dry atmosphere. At the end of the final nitrogen purge, the pressure was adjusted to be slightly above one atmosphere.

The vessel was heated by setting the oil controller at 195° C. at a rate of 180° C. per hour. The reaction continued for 2.5 hours from the time the oil temperature reached 195° C.

In the next stage, the oil controller set point was decreased first to 150° C., and 27,586 grams of molten p-dioxanone monomer was added from a melt tank with the agitator speed of 10 RPM. The reactor temperature was than lowered to 110° C. for the rest of the reaction with the agitator speed of 7.5 RPM in a forward direction for 240 minutes. At the end of the reaction, the agitator speed was reduced to 5 RPM, and the polymer was discharged from the vessel into suitable containers. The containers were placed into a nitrogen oven set at 80° C., and the resin (28.57 kg) was cured in the solid state for additional 124 hours. During this step, the constant nitrogen flow was maintained in the oven to reduce possible moisture-induced degradation.

The polymer was then removed from the containers and placed into a freezer set at approximately −20° C. for a minimum of 24 hours. The polymer was then subjected to grinding, sieving, and drying procedures identical to those in the previous examples.

The resin was stored under vacuum. The dried resin exhibited an inherent viscosity of 1.21 dL/g, as measured in hexafluoroisopropanol at 25° C. and at a concentration of 0.10 g/dL. Gel permeation chromatography analysis showed a weight average molecular weight of approximately 51,000 Daltons. Nuclear magnetic resonance analysis confirmed that the resin contained 92.7 mole percent poly(p-dioxanone) and 6.0 mole percent poly(epsilon-caprolactone) with a residual monomer content of 1.4 percent. The dried polymer was stored under vacuum until ready for use or evaluation.

Example 6A (Non-Inventive, Too High Level of Polymerized Epsilon-Caprolactone)

Synthesis of Segmented p-Dioxanone-Rich Poly(p-Dioxanone-Co-Epsilon-Caprolactone) A-B-A Triblock Copolymer at 74/26 by Mole, Wherein the "B" Segment is Composed 66 Mole % Polymerized Epsilon-Caprolactone and 34 Mole % Polymerized p-Dioxanone The synthesis of this polymer was conducted in the similar fashion as in previous examples, except that the higher level of epsilon-caprolactone was used to make the final copolymer. Also, the polymer was then subjected to grinding, sieving, and drying procedures identical to those in the previous examples.

The resin was stored under vacuum. The dried resin exhibited an inherent viscosity of 0.93 dL/g, as measured in hexafluoroisopropanol at 25° C. and at a concentration of 0.10 g/dL. Gel permeation chromatography analysis showed a weight average molecular weight of approximately 31,000 Daltons. Nuclear magnetic resonance analysis confirmed that the resin contained 73.5 mole percent poly(p-dioxanone) and 26.4 mole percent poly(epsilon-caprolactone) with a residual monomer content of 0.1 percent. The dried polymer was stored under vacuum until ready for use or evaluation.

Example 6B (Non-Inventive)

Monofilament Extrusion of the Segmented p-Dioxanone-Rich Poly(p-Dioxanone-Co-Epsilon-Caprolactone) Triblock Copolymer of Example 6A (74/26 by Mole, with "B" Block Composition Cap/PDO 66/34 by Mole)

The copolymer of Example 6A was extruded using a single-screw Davis-Standard one inch extruder with a 24:1 barrel length equipped with a single grooved feed throat. The die had a diameter of 60 mils and an L/D of 5/1; the die temperature was 110° C. After passing through an air gap of ¼ inch, the extrudate was quenched in a 20° C. water bath.

After exiting water bath, the fiber went to an air quench cabinet maintained at 85° F. with four to eight wraps. The fiber line was then directed toward a first set of unheated godet rolls at a linear speed of 20 fpm. The fiber line next went through 4-foot hot air oven at 70° C. located right between first and second sets of godets. The fiber line was then directed toward the second set of unheated godets operating at 118 fpm. The fiber line was then directed through a 6-foot hot air oven at 90° C. to a third set of unheated godet rolls; this set of rolls was operating at 135 fpm. The line was then directed through a second 6-foot hot air oven at 90° C. to a fourth set of unheated godet rolls. This last set of rolls was operating at 131 fpm, which is a lower speed than the previous set of godet rollers allowing the fiber to relax slightly (3.0%). The overall draw ratio was 6.55.

This monofilament extrusion for the resin of Example 4A went smoothly, but lower crystallinity levels produced very soft and weak fibers. Prior to testing, the fiber was also annealed at 85° C. for six hours on straight rack (0% rack relaxation).

Example 7

Calorimetric Properties of Inventive and Non-Inventive Monofilaments calorimetric properties of the monofilaments made from the inventive and non-inventive compositions were determined by Differential Scanning calorimetry, DSC. calorimetric results were generated on a TA Instruments Differential Scanning calorimeter, Model 2910 MDSC, using dry N2 as a purge gas. In this study, the first and second heat scans were conducted. For the first heat measurements, the copolymers (5-10 mg) were first quenched below their glass transition temperatures and then heated under a controlled heating rate of 10° C./min. From the first heat measurements one can learn about the "as is" thermal properties of the fiber, including the thermal history. For the second heat measurements, after melting of the copolymers at 140° C. for three minutes, the copolymers were quenched below their glass transition temperatures, and then heated under a controlled heating rate of 10° C./min. From the second heat measurements one can learn about inherent properties of the fiber or its resin, regardless of the thermal history. A Summary of data is presented in Table 1.

TABLE 1

DSC Data of Unannealed and Annealed Monofilaments Made from Inventive and Non-Inventive Compositions

| | First heat | | | Second heat | | | | |
|---|---|---|---|---|---|---|---|---|
| Fiber ID | $T_g$ (° C.) | $T_m$ (° C.) | $\Delta H_m$ (J/g) | $T_g$ (° C.) | $T_c$ (° C.) | $\Delta H_c$ (J/g) | $T_m$ (° C.) | $\Delta H_m$ (J/g) |
| Ex. 1B - Unannealed | −2 | 53/102 | 81 | −9 | 16 | 20 | 52/105 | 46 |
| Ex. 1B - Annealed | −1 | 52/101 | 94 | −9 | 16 | 19 | 52/105 | 44 |
| Ex. 2B - Unannealed | 0 | 50/103 | 62 | −11 | 14 | 18 | 48/103 | 54 |
| Ex. 2B - Annealed | 2 | 51/102 | 84 | −10 | 15 | 18 | 49/102 | 53 |

TABLE 1-continued

DSC Data of Unannealed and Annealed Monofilaments
Made from Inventive and Non-Inventive Compositions

| Fiber ID | First heat | | | Second heat | | | | |
|---|---|---|---|---|---|---|---|---|
| | $T_g$ (° C.) | $T_m$ (° C.) | $\Delta H_m$ (J/g) | $T_g$ (° C.) | $T_c$ (° C.) | $\Delta H_c$ (J/g) | $T_m$ (° C.) | $\Delta H_m$ (J/g) |
| Ex. 3B - Unannealed | −6 | 103 | 72 | −11 | 35 | 38 | 104 | 44 |
| Ex. 3B - Annealed | −3 | 104 | 72 | −12 | 34 | 39 | 102 | 47 |
| Ex. 4B - Unannealed | −7 | 103 | 61 | −12 | 32 | 37 | 103 | 46 |
| Ex. 4B - Annealed | −5 | 103 | 67 | −12 | 30 | 37 | 103 | 47 |
| Ex. 6B - Unannealed | −8 | 103 | 52 | −13 | 29 | 34 | 104 | 44 |
| Ex. 6B - Annealed | −10 | 104 | 65 | −13 | 28 | 35 | 104 | 45 |

Figure 1:
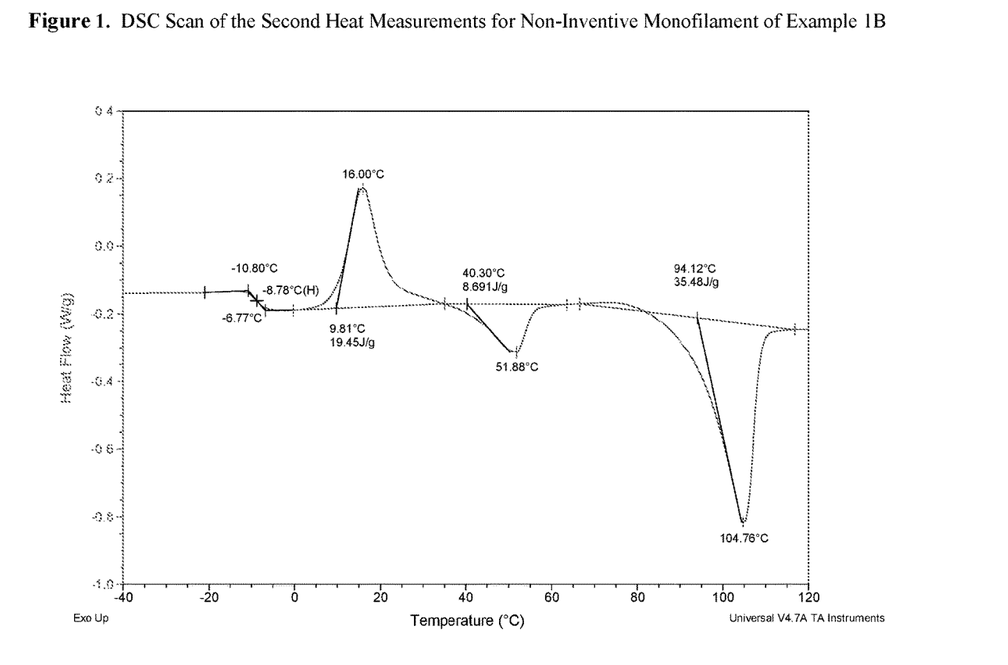
FIG. 1 is a DSC Scan of the Second Heat Measurements for the Non-Inventive Monofilament of Example 1B
Figure 2:
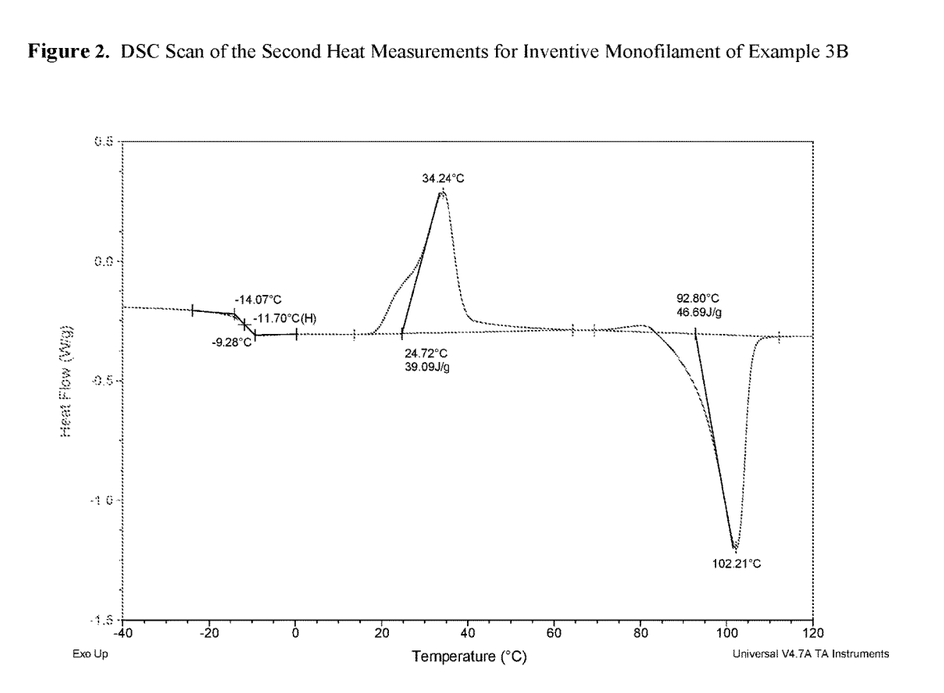
FIG. 2 is a DSC Scan of the Second Heat Measurements for the Inventive Monofilament of Example 3B

Surprisingly, it was found that the monofilaments made from the non-inventive Examples 1 and 2 have a lower melting peak located at about 50° C. for unannealed and annealed monofilaments, as well in scans of their starting resins (data not shown here). This a clear signature of polymerized epsilon-caprolactone segments of the "B" block that crystallized side-by-side with polymerized p-dioxanone segments of the "A" block. As an illustration, the DSC trace of the second scan of the non-inventive, annealed Example 1B is shown in FIG. 1. In contrast, the DSC trace of the second scan of the inventive, annealed Example 3B, shown in FIG. 2, did not show any signs of crystallization for polymerized epsilon-caprolactone segments. Additional supporting data from Wide Angle X-ray Diffraction conducted on all inventive and non-inventive Examples proved that the crystallization of epsilon-caprolactone segments were always present in the non-inventive Examples 1 and 2, but absent in inventive Examples 3 and 4.

The fact that the "B" block in non-inventive Examples 1 and 2 is crystallizable is surprising and unexpected considering the short length of that segment compared to p-dioxanone-rich "A" block. Most importantly, a practical disadvantage of the crystalline "B" block is in increased stiffness and higher Young's Modulus of elasticity for the resulting fibers as will be shown in the next Example 8.

Example 8

Physical Properties of Inventive and Non-Inventive Monofilaments

As discussed in Examples 3B and 4B, the monofilament extrusion for the fibers of the present invention went smoothly, with fibers that appeared to be very smooth, pliable yet strong. Tensile properties were determined using an Instron testing machine on the unannealed and annealed monofilaments of the present invention (Ex. 3 and 4), as well as unannealed and annealed monofilaments made by non-inventive compositions (Ex. 1, 2 and 6). The gage length was 5 inches; a sampling rate of 20 pts/secs with a crosshead speed of 12 in/min was employed. The full scale load range was 100 lbf. Selected tensile properties (mean values) are listed In Table 2. Knot tensile measurements were made with a single knot made in the middle of the thread.

TABLE 2

Tensile Properties of Unannealed and Annealed 2-0 Monofilaments
Made from Inventive and Non-Inventive Compositions

| Example ID | Diameter (Mils) | Annealing Conditions | Final Draw Ratio | Straight Tensile (Lbs) | Elong. (%) | Knot Tensile (Lbs) | Young's Modulus (Kpsi) |
|---|---|---|---|---|---|---|---|
| 1B-1 | 14.37 | None | 7.6x | 9.9 | 36 | 6.6 | 141 |
| 1B-2 | 14.25 | 85° C./6 hrs | 7.6x | 10.3 | 36 | 6.8 | 178 |
| 2B-1 | 14.22 | None | 6.2x | 11.0 | 30 | 6.8 | 157 |
| 2B-2 | 14.26 | 85° C./6 hrs | 6.2x | 11.3 | 31 | 6.4 | 194 |
| 3B-1 | 14.40 | None | 5.9x | 10.3 | 30 | 6.6 | 107 |
| 3B-2 | 14.36 | 85° C./6 hrs | 5.9x | 10.5 | 31 | 6.4 | 151 |
| 4B-1 | 14.36 | None | 6.4x | 10.0 | 30 | 6.6 | 90 |
| 4B-2 | 14.36 | 85° C./6 hrs | 6.4x | 10.0 | 33 | 6.2 | 89 |
| 6B-1 | 14.35 | None | 6.6x | 4.4 | 49 | 3.0 | 44 |
| 6B-2 | 14.34 | 85° C./6 hrs | 6.6x | 4.4 | 47 | 3.1 | 55 |

Several important conclusions can be drawn from data in Table 2. Non-inventive monofilament from Example 6B showed very low tensile properties due to a large amount of polymerized epsilon-caprolactone in the structure. The overall crystallinity level found for the annealed sample 6B-2 was only 27% as determined by WAXD.

The rest of the samples in Table 2 including non-inventive and inventive, unannealed and annealed fibers showed comparable fiber strength; straight tensile between about 10 to about 11 pounds, knot strength around 6.5 pounds, and elongation values between 30 and 36%. However, the major difference in physical properties was in elasticity, softness or pliability of the fibers, as determined by Young's Modulus values (last column in Table 2). Regardless of the total amount of polymerized epsilon-caprolactone present in the structure, the monofilaments made by the copolymers of the present invention exhibited significantly lower Young's Modulus values than the corresponding non-inventive monofilaments made by copolymers where the "B" block was composed of polymerized epsilon-caprolactone only.

In order to further describe the key properties of the copolymers and monofilaments of the present invention, presented in Table 3 below is a wide range of physical properties data on the monofilaments of the present invention, non-inventive monofilaments, as well as corresponding data from the closest prior art (Bezwada '048) and data from p-dioxanone homopolymer as a control.

TABLE 3

Mechanical Properties of Annealed PDO/CAP Triblock
(ABA) Monofilaments and PDS Suture as a Control

| Fiber ID | Ex. 1 (non-inventive) | Ex. 2 (non-inventive) | Ex. 3 (inventive) | Ex. 4 (inventive) | Bezwada '048 Ex. 3 | Bezwada '048 Ex. 2 | PDS Control from '048 |
|---|---|---|---|---|---|---|---|
| PDO/PCL overall composition (wt. %) | 78/22 | 82/18 | 85/15 | 80/20 | 80/20 | 90/10 | 100% |

TABLE 3-continued

Mechanical Properties of Annealed PDO/CAP Triblock
(ABA) Monofilaments and PDS Suture as a Control

| Fiber ID | Ex. 1 (non-inventive) | Ex. 2 (non-inventive) | Ex. 3 (inventive) | Ex. 4 (inventive) | Bezwada '048 Ex. 3 | Bezwada '048 Ex. 2 | PDS Control from '048 |
|---|---|---|---|---|---|---|---|
| Center block, B composition (mole %) | 100% PCL | 100% PCL | 66/34 PCL/PDO | 66/34 PCL/PDO | 100% PCL | 100% PCL | NA |
| IV (dL/g) | 1.43 | 1.20 | 1.86 | 1.20 | 1.82 | 2.47 | 1.88 |
| $T_g$ (° C.) | −1 | 2 | −3 | −5 | NA | NA | 1* |
| Melting point (° C.) | 52 & 103 | 51 & 102 | 104 | 103 | 106 | 104 | 109 |
| % Cryst. by WAXD | 46 | 51 | 38 | 34 | NA | NA | 58* |
| Straight tensile strength (Kpsi) | 65 | 71 | 65 | 62 | 73 | 90 | 74 |
| Knot tensile strength (Kpsi) | 43 | 41 | 40 | 39 | 55 | 56 | 55 |
| Percent elongation | 36 | 31 | 31 | 33 | 32 | 35 | 29 |
| Young's Modulus (Kpsi) | 178 | 194 | 151 | 89 | 298 | 271 | 324 |
| BSR (%) @ 21 days | 44 | 74 | 85 | 55 | NA | NA | 70 |
| BSR (%) @ 90 days | NA | NA | 11 | NA | NA | NA | 5* |

*additional data obtained in our lab on the commercial 2-0 PDS suture taken directly from the package In Table 3 the physical properties of various p-dioxanone-rich poly(p-dioxanone-co-epsilon-caprolactone) triblock copolymer compositions were given including molecular weights, percent of crystallinity, tensile and hydrolytic (BSR) data. Looking at the comparable overall chemical compositions (e.g. 80/20 PDO/Cap, columns 3, 5, and 6), the annealed monofilaments of the present invention exhibit significantly lower Young's modulus of elasticity—89 compared to 194 and 298 kpsi, both obtained by the method where "B" block is composed of 100% epsilon-caprolactone. The annealed monofilaments of the present invention also contain lower crystallinity levels and lower glass transition temperatures due to the fact that "B" block is fully amorphous. It should be noted that Bezwada et al. ('048) were not aware that their copolymers contain center block "B" that is crystalline. They used much less sensitive instruments to characterize thermal properties (optical microscopy vs. DSC or WAXD), which were not capable of detecting secondary melting transition of epsilon-caprolactone segments.

Hydrolytic, in vitro BSR properties (last two rows of Table 3) appeared to be a strong function of total epsilon-caprolactone level of copolymers, molecular weight, and percent of crystallinity. Monofilaments listed in Table 3 having around 15 wt. % or less polymerized epsilon-caprolactone, and also possessing higher Mw or IV, with higher total crystallinity levels tend to display longer in vitro breaking strength retention values. The inventive 85/15 PDO/Cap monofilament with 34/66 PDO/Cap center block "B" (fourth column in Table 3) exhibited the longest BSR profile, longer even than p-dioxanone homopolymer.

To briefly summarize, the novel absorbable copolymers of the present invention and novel medical devices made from such copolymers have numerous advantages. The advantages include the following: extraordinary softness and pliability of the fibers; extended breaking strength retention profile; can be made into a monofilament; low tissue reaction; easier to pull through tissue; lesser tissue drag; believed to have better moldability; dimensional stability; and expected improved photostability vs. poly(p-dioxanone) homopolymer. The copolymers are readily made into long-term absorbable sutures having superior properties, both monofilament and braided constructions.

Although this invention has been shown and described with respect to detailed embodiments thereof, it will be understood by those skilled in the art that various changes in form and detail thereof may be made without departing from the spirit and scope of the claimed invention.

We claim:

1. An absorbable copolymer of the structure A-B-A comprising end segments A and middle segment B, wherein end-segments A comprise polymerized p-dioxanone blocks and the middle segment B is a copolymer comprising a polymerized p-dioxanone-co-epsilon-caprolactone block, and wherein said middle segment B is fully amorphous and contains about 60 mole percent to about 90 mole percent of polymerized epsilon-caprolactone, and about 10 mole percent to about 40 mole percent of polymerized p-dioxanone, and wherein the total amount of polymerized p-dioxanone in the absorbable copolymer is between about 80 mole percent to about 95 mole percent.

2. The absorbable copolymer of claim 1, having an inherent viscosity, IV greater than 1.0 dl/g, and a weight average molecular weight, Mw greater than 30,000 Daltons.

3. The absorbable copolymer of claim 1, having a crystallinity level greater than 30% as measured by wide angle X-ray diffraction, WAXD.

4. The absorbable copolymer of claim 1, containing less than 20 mole % epsilon-caprolactone.

5. An absorbable medical device, comprising: an absorbable copolymer of the structure A-B-A comprising end segments A and middle segment B, wherein end-segments A comprise polymerized p-dioxanone blocks and the middle segment B is a copolymer comprising a polymerized p-dioxanone-co-epsilon-caprolactone block, and wherein said middle segment B is fully amorphous and contains about 60 mole percent to about 90 mole percent of polymerized epsilon-caprolactone, and about 10 mole percent to about 40 mole percent of polymerized p-dioxanone, and wherein the total amount of polymerized p-dioxanone in the absorbable copolymer is between about 80 mole percent to about 95 mole percent.

6. The absorbable medical device of claim 5, wherein said device is selected from the group consisting of monofilaments, monofilament sutures, multifilament sutures, surgical meshes, surgical fabrics, films, barbed sutures, and injection molded articles.

7. The absorbable medical device of claim 6, wherein said medical device comprises an absorbable monofilament suture.

8. The absorbable monofilament suture of claim 7, having a Young's modulus less than about 200 Kpsi.

9. The absorbable monofilament suture of claim 7, having a Young's modulus less than about 160 Kpsi.

10. The absorbable monofilament suture of claim 7, having a BSR higher that 50% at 21 days.

11. The absorbable monofilament suture of claim 7, having a straight tensile strength of higher than 50 Kpsi.

12. The absorbable monofilament suture of claim 7, additionally comprising at least one barb.

13. The medical device of claim 5, additionally comprising an antimicrobial agent.

14. The medical device of claim 5, additionally comprising a therapeutic agent.

15. The medical device of claim 5, additionally comprising a dye.

16. The medical device of claim 5, additionally comprising a medically useful substance.

17. An absorbable copolymer of the structure A-B-A comprising end segments A and middle segment B, wherein end-segments A comprise polymerized p-dioxanone blocks and the middle segment B is a copolymer comprising epsilon-caprolactone and a minor amount of a lactone monomer selected from the group consisting of L(-)-lactide, D(+)-lactide, meso-lactide, and trimethylene carbonate, and wherein said middle segment B is fully amorphous and contains about 60 mole percent to about 95 mole percent of polymerized epsilon-caprolactone, and about 5 mole percent to about 40 mole percent of polymerized lactone monomer, and wherein the total amount of polymerized p-dioxanone in the absorbable copolymer is between about 80 mole percent to about 95 mole percent.

18. The absorbable polymer of claim 17 wherein the "B" segment contains between 5 mole % and 15 mole % polymerized L(-)-lactide.

19. The absorbable polymer of claim 17, wherein the lactone monomer comprises trimethylene carbonate.

20. The medical device of claim 5, wherein said device is manufactured by a process selected from the group consisting of extrusion, melt processing, and injection molding.

* * * * *